(12) United States Patent
Gale et al.

(10) Patent No.: US 8,267,990 B2
(45) Date of Patent: Sep. 18, 2012

(54) CONTROLLED DEGRADATION OF STENTS

(75) Inventors: David C. Gale, San Jose, CA (US); Bin Huang, Pleasanton, CA (US); Vincent Gueriguian, San Francisco, CA (US); Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 207 days.

(21) Appl. No.: 12/872,166

(22) Filed: Aug. 31, 2010

(65) Prior Publication Data

US 2011/0098803 A1    Apr. 28, 2011

Related U.S. Application Data

(62) Division of application No. 11/488,928, filed on Jul. 17, 2006, now Pat. No. 7,794,495.

(51) Int. Cl.
*A61F 2/82* (2006.01)

(52) U.S. Cl. .............. 623/1.38; 604/93.01; 427/2.24; 623/1.44

(58) Field of Classification Search ............. 427/2.24; 623/1.15, 1.38–1.46; *A61F 2/82*
See application file for complete search history.

(56) References Cited

U.S. PATENT DOCUMENTS

| | | | |
|---|---|---|---|
| 3,467,690 A | 9/1969 | Chamberlin | |
| 4,181,983 A | 1/1980 | Kulkarni | |
| 4,839,130 A | 6/1989 | Kaplan et al. | |
| 4,844,854 A | 7/1989 | Kaplan et al. | |
| 5,007,923 A | 4/1991 | Bezwada et al. | |
| 5,085,629 A | 2/1992 | Goldberg et al. | |
| 5,124,103 A | 6/1992 | Kaplan et al. | |
| 5,225,521 A | 7/1993 | Spinu | |
| 5,434,241 A | 7/1995 | Kim et al. | |
| 5,464,929 A | 11/1995 | Bezwada et al. | |
| 5,641,501 A | 6/1997 | Cooper et al. | |
| 5,641,745 A | 6/1997 | Ramtoola | |
| 5,696,178 A | 12/1997 | Cooper et al. | |
| 5,705,181 A | 1/1998 | Cooper et al. | |
| 5,922,338 A | 7/1999 | Brich et al. | |
| 5,957,975 A | 9/1999 | Lafont et al. | |
| 6,025,458 A | 2/2000 | Lipinsky et al. | |
| 6,201,072 B1 | 3/2001 | Rathi et al. | |
| 6,211,249 B1 | 4/2001 | Cohn et al. | |
| 6,221,977 B1 | 4/2001 | Park et al. | |
| 6,323,307 B1 | 11/2001 | Bigg et al. | |
| 6,362,308 B1 | 3/2002 | Pham | |
| 6,423,092 B2 | 7/2002 | Datta et al. | |
| 6,485,749 B1 | 11/2002 | Shalaby | |
| 6,498,229 B1 | 12/2002 | Shalaby | |
| 6,544,223 B1 | 4/2003 | Kokish | |

(Continued)

FOREIGN PATENT DOCUMENTS

WO    WO 03/080147    10/2003

(Continued)

OTHER PUBLICATIONS

Invitation to Pay Additional Fees for PCT/US2007/016243, mailed Oct. 28, 2008, 5 pgs.

(Continued)

*Primary Examiner* — Thomas J Sweet
*Assistant Examiner* — Jason-Dennis Stewart
(74) *Attorney, Agent, or Firm* — Squire Sanders (US) LLP

(57) ABSTRACT

Stents fabricated from hydrolytically degradable polymers with accelerated degradation rates and methods of fabricating stents with accelerated degradation rates are disclosed.

16 Claims, 10 Drawing Sheets

U.S. PATENT DOCUMENTS

| | | |
|---|---|---|
| 6,770,729 B2 | 8/2004 | Van Antwerp |
| 7,074,883 B2 | 7/2006 | Pham |
| 7,094,862 B2 | 8/2006 | Cazaux et al. |
| 7,202,325 B2 | 4/2007 | Pacetti et al. |
| 7,311,980 B1 | 12/2007 | Hossainy et al. |
| 2001/0009662 A1 | 7/2001 | Cohn et al. |
| 2001/0032008 A1 | 10/2001 | Wang et al. |
| 2002/0016596 A1 | 2/2002 | Cooper |
| 2002/0062147 A1 | 5/2002 | Yang |
| 2002/0086971 A1 | 7/2002 | Pham |
| 2002/0090398 A1 | 7/2002 | Dunn et al. |
| 2003/0012734 A1 | 1/2003 | Pathak et al. |
| 2003/0027940 A1 | 2/2003 | Lang et al. |
| 2003/0105245 A1 | 6/2003 | Amsden |
| 2003/0139567 A1 | 7/2003 | Kim et al. |
| 2003/0152546 A1 | 8/2003 | Shalaby |
| 2003/0211131 A1 | 11/2003 | Martin et al. |
| 2004/0030262 A1 | 2/2004 | Fisher et al. |
| 2004/0084804 A1 | 5/2004 | John |
| 2004/0084805 A1 | 5/2004 | John |
| 2004/0093077 A1 | 5/2004 | White et al. |
| 2004/0122511 A1 | 6/2004 | Mangiardi et al. |
| 2004/0127974 A1 | 7/2004 | Mangiardi et al. |
| 2004/0230298 A1 | 11/2004 | Udipi et al. |
| 2004/0242722 A1 | 12/2004 | Rose et al. |
| 2005/0025799 A1 | 2/2005 | Hossainy et al. |
| 2005/0107531 A1 | 5/2005 | Claude |
| 2005/0112170 A1 | 5/2005 | Hossainy et al. |
| 2005/0124782 A1 | 6/2005 | Takamura et al. |
| 2005/0149175 A1 | 7/2005 | Hunter et al. |
| 2005/0186245 A1 | 8/2005 | Hunter et al. |
| 2005/0238689 A1 | 10/2005 | Carpenter et al. |
| 2006/0013849 A1 | 1/2006 | Strickler et al. |
| 2006/0029637 A1 | 2/2006 | Tice et al. |
| 2006/0041102 A1 | 2/2006 | Hossainy et al. |
| 2006/0045901 A1 | 3/2006 | Weber |
| 2006/0095122 A1 | 5/2006 | Pacetti |
| 2006/0160985 A1 | 7/2006 | Pacetti et al. |
| 2006/0171980 A1 | 8/2006 | Helmus et al. |
| 2006/0269590 A1 | 11/2006 | Trotter et al. |
| 2007/0003625 A1 | 1/2007 | Seo et al. |
| 2007/0005130 A1 | 1/2007 | Glauser et al. |
| 2007/0043434 A1 | 2/2007 | Meerkin et al. |
| 2007/0200271 A1 | 8/2007 | Dave |
| 2007/0207179 A1 | 9/2007 | Andersen et al. |
| 2007/0224234 A1 | 9/2007 | Steckel et al. |
| 2007/0254012 A1 | 11/2007 | Ludwig et al. |
| 2007/0258903 A1 | 11/2007 | Kleiner et al. |
| 2007/0269485 A1 | 11/2007 | Richard et al. |
| 2007/0282435 A1 | 12/2007 | Wang et al. |
| 2007/0286883 A1 | 12/2007 | Lensen et al. |
| 2007/0299504 A1 | 12/2007 | Gale et al. |
| 2008/0004400 A1 | 1/2008 | Hossainy et al. |
| 2008/0015686 A1 | 1/2008 | Gale et al. |
| 2008/0063685 A1 | 3/2008 | Wang et al. |
| 2008/0147165 A1 | 6/2008 | Hossainy et al. |
| 2008/0199506 A1 | 8/2008 | Horres et al. |
| 2008/0221265 A1 | 9/2008 | Sodergard et al. |
| 2008/0243228 A1 | 10/2008 | Wang et al. |
| 2008/0249614 A1 | 10/2008 | Wang et al. |
| 2008/0299164 A1 | 12/2008 | Trollsas |
| 2008/0306582 A1 | 12/2008 | Wang et al. |
| 2008/0306591 A1 | 12/2008 | Wang et al. |
| 2009/0095715 A1 | 4/2009 | Sabaria |
| 2009/0247666 A1 | 10/2009 | Yu et al. |
| 2009/0306120 A1 | 12/2009 | Lim et al. |
| 2009/0319036 A1 | 12/2009 | Wang et al. |

FOREIGN PATENT DOCUMENTS

| | | |
|---|---|---|
| WO | WO 2005/115493 | 12/2005 |

OTHER PUBLICATIONS

Biela et al., "Star-Shaped Poly(L-lactide)s with Variable Numbers of Hydroxyl Groups at Polyester Arms Chain-Ends and Directly Attached to the Star-Shaped Core-Controlled Synthesis and Characterization", J. of Polymer Science vol. 43, pp. 6116-6133 (2005).

He et al., "Synthesis and cell affinity of functionalized poly(L-lactide-co-β-malic acid) with high molecular weight" Biomaterials 25, pp. 5239-5247 (2004).

Middleton et al., "Synthetic biodegradable polymers as orthopedic devices", Biomaterials 21, pp. 2335-2346 (2000).

PLGA-PEG Copolymers, Drug Delivery vol. 3, No. 5, 10 pg. (2003).

Zhao et al., "Synthesis and Characterization of Star-Shaped Poly(L-lactide)s Initiated with Hydroxyl-Terminated Poly(Amidoamine)) (PAMAM-OH) Dendrimers", Chem. Mater 15, pp. 2836-2843 (2003).

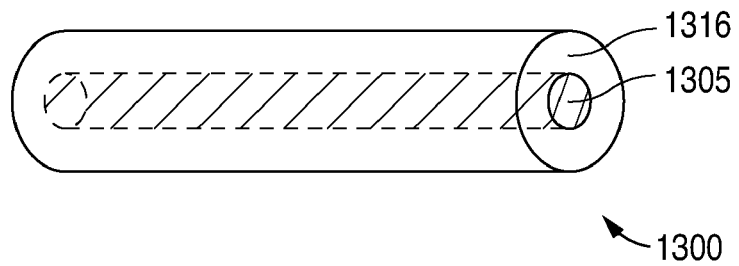
FIG. 13
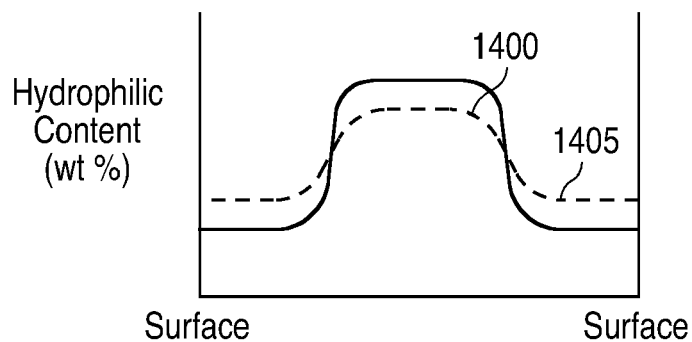
FIG. 14A
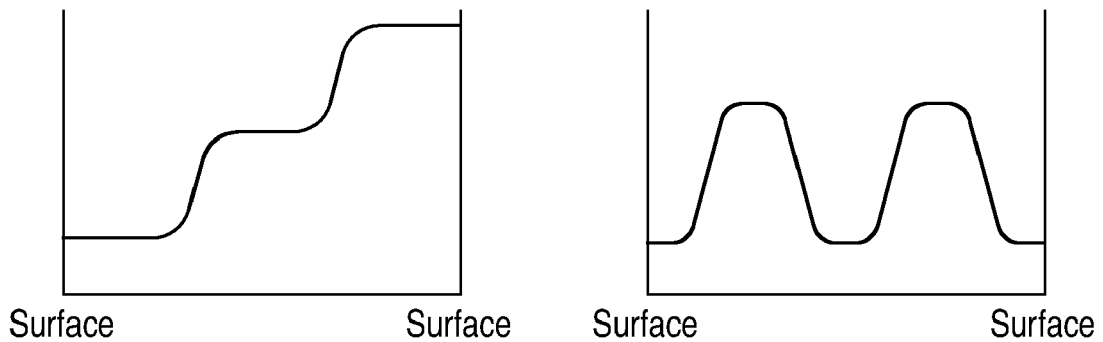
FIG. 14C  FIG. 14B

CONTROLLED DEGRADATION OF STENTS

RELATED APPLICATIONS

This application is a divisional application of U.S. patent application Ser. No. 11/488,928, filed 17 Jul. 2006, which is incorporated by reference as if fully set forth, including any figures, herein.

BACKGROUND OF THE INVENTION

1. Field of the Invention

This invention relates to controlled degradation of implantable medical devices, such as stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended. However, some biodegradable polymers have degradation rates that are slower than desired. As a result, stents fabricated from such biodegradable polymers will remain in the body after the clinical need for them has ended.

SUMMARY OF THE INVENTION

Certain embodiments of the present invention include a method of fabricating a biodegradable polymer stent comprising: forming a biodegradable polymer with a polymerization that is initiated with an acid containing group, the formed polymer including at least one acid group from the initiator; and fabricating a stent from the formed polymer.

Further embodiments of the present invention include a method of fabricating a biodegradable polymer stent comprising: forming an intermediate polymer comprising a chain with a plurality of hydrolytically degradable functional groups and an acidic end group at one end of the chain; forming an end-product polymer through addition of another acidic end group at the other end of the chain; and fabricating a stent from the end-product polymer.

Additional embodiments of the present invention include a method of fabricating a biodegradable polymer stent comprising: obtaining a star-shaped or dendritic intermediate polymer comprising at least three chains, the at least three chains comprising a plurality of hydrolytically degradable functional groups; forming an end-product polymer through addition of an acidic end group at the end of at least one of the three chains; and fabricating a stent from the end-product polymer.

Other embodiments of the present invention include a method of fabricating a biodegradable polymer stent comprising: forming an intermediate polymer comprising a backbone having a plurality side chains, the backbone and side chains comprising a plurality of hydrolytically degradable functional groups; forming an end-product polymer from the intermediate polymer, the end-product polymer having an acidic end group at the end of at least one of the side chains; and fabricating a stent from the end product polymer.

Some embodiments of the present invention include a method of fabricating a biodegradable polymer stent comprising: forming a biodegradable polymer comprising a polymer backbone having a plurality of acid containing pendant groups along the backbone, the polymer backbone comprising a plurality of hydrolytically degradable functional groups; and fabricating a stent from polymer.

Additional embodiments of the present invention include a stent comprising a structural element, the structural element comprising a polymer including: a hydrolytically degradable polymer having at least one acid end group, wherein the polymer is selected from the group consisting of: an unbranched polymer having an acid end group at each end; a star-shaped or dendritic polymer comprising at least three chains including the hydrolytically degradable functional groups, at least one of the chains having an acid end group; a polymer with a backbone having a plurality side chains having a plurality of hydrolytically degradable functional groups, at least one of the side chains having an acid end group; a polymer with a backbone having a plurality of acid containing pendant groups along the backbone, and any combination thereof.

Further embodiments of the present invention include a stent comprising a structural element, the structural element comprising a block copolymer including: a hydrolytically degradable polymer block; and at least one acidic polymer block including a plurality of pendant acid groups, the acidic polymer block being capable of cleaving from the hydrolytically degradable polymer block upon exposure to bodily fluids.

Additional embodiments of the present invention include a stent comprising a structural element, the structural element comprising a block polymer including: a hydrolytically degradable polymer block; and at least one acidic polymer block including a pendant acid group bonded to a radiation sensitive protecting group, the acidic polymer block capable of cleaving from the polymer upon exposure to bodily fluids.

Certain embodiments of the present invention include a stent comprising a structural element, the structural element comprising a polymer blend including poly(L-lactide) blended with a block copolymer comprising a poly(L-lactide) block and at least one acidic polymer block, the acidic polymer block including a plurality of pendant acid groups.

Some embodiments of the present invention include a stent comprising a structural element, the structural element comprising a polymer blend including poly(L-lactide) blended with a block copolymer comprising poly(L-lactide) and at least one acidic polymer block, the acidic polymer block including a pendant acid group bonded to a radiation sensitive protecting group.

Further embodiments of the present invention include a stent comprising a structural element, the structural element comprising a polymer blend including: poly(L-lactide); and a block copolymer blended with the poly(L-lactide), the block copolymer comprising a poly(L-lactide) block and at least one acidic polymer block, wherein the acidic polymer block phase separates from the poly(L-lactide).

Additional embodiments of the present invention include a stent comprising a structural element, the structural element comprising a hydrolytically degradable polymer, the polymer having a star-shaped or dendritic structure.

Further embodiments of the present invention include a stent comprising a structural element, the structural element comprising a polymer blend including: a linear hydrolytically degradable polymer; and a hydrolytically degradable star-shaped and/or dendritic polymer, the star-shaped and/or dendritic polymers inhibiting or preventing formation of crystalline domains in the structural element.

Some embodiments of the present invention include a method of fabricating a stent comprising: forming a structural element comprising a polymer blend including a linear hydrolytically degradable polymer and a hydrolytically degradable star-shaped and/or dendritic polymer; and selecting the star-shaped and/or dendritic polymers having properties that obtain a desired degradation rate of the polymer blend.

Other embodiments of the present invention include a stent comprising a structural element, the structural element comprising a polymer including: a block copolymer comprising a hydrolytically degradable polymer block and a hydrophilic polymer block.

Additional embodiments of the present invention include a stent comprising a structural element, the structural element comprising a polymer blend including: a hydrolytically degradable polymer; and a block copolymer blended with the hydrolytically degradable polymer, the block copolymer comprising a hydrolytically degradable polymer block and a hydrophilic polymer block.

Further embodiments of the present invention include a stent comprising a structural element, the structural element comprising: an inner region and an outer region, the inner region and the outer region comprising a hydrolytically degradable polymer, a hydrophilic polymer, and/or a block copolymer including a hydrolytically degradable polymer block and a hydrophilic polymer block, wherein the inner region has a higher hydrophilic polymer content than the outer region.

Some embodiments of the present invention include a stent comprising a structural element, the structural element comprising a polymer blend including: a slow degrading hydrolytically degradable polymer; and a fast degrading hydrolytically degradable polymer, the fast degrading polymer having a substantially faster degradation rate than the slow degrading polymer, wherein the degradation products of the fast degrading polymer are acidic and hydrophilic, the acidic degradation products being capable of increasing the degradation rate of the slow degrading polymer.

Additional embodiments of the present invention include a method of treating a bodily lumen comprising: releasing an acidic agent at or adjacent to a hydrolytically degradable polymer stent implanted within a bodily lumen, the acidic agent lowers the pH of bodily fluid at or adjacent to the stent, the lowered pH of the bodily fluid increases the degradation rate of the stent.

Other embodiments of the present invention include a method of treating a bodily lumen comprising: positioning a delivery device within a bodily lumen at or adjacent to a hydrolytically degradable polymer stent implanted within the bodily lumen; disposing an acidic agent into the delivery device; releasing the acidic agent from the delivery device into the bodily lumen, wherein the released acidic agent lowers the pH of the bodily fluid at or adjacent to the stent below physiological pH which increases the degradation rate of the stent.

BRIEF DESCRIPTION OF THE DRAWINGS

FIG. 13 depicts a portion of a cylindrical structural element having an inner core region surrounded by an outer region.

FIG. 14A depicts two hydrophilic content distributions through a cross-section of a structural element.

FIG. 14B depicts a bimodal distribution of hydrophilic content.

FIG. 14C depicts a hydrophilic distribution that increases from one outer region to another in a step-function fashion.

DETAILED DESCRIPTION OF THE INVENTION

The various embodiments of the present invention relate to modifying or controlling the degradation of implantable medical devices that are fabricating in whole or in part from biodegradable polymers. Embodiments involve controlling or modifying the degradation rate and degradation time of biodegradable devices. The present invention can be applied to implantable medical devices including, but not limited to, self-expandable stents, balloon-expandable stents, stent-grafts, and grafts (e.g., aortic grafts).

Figure 1:
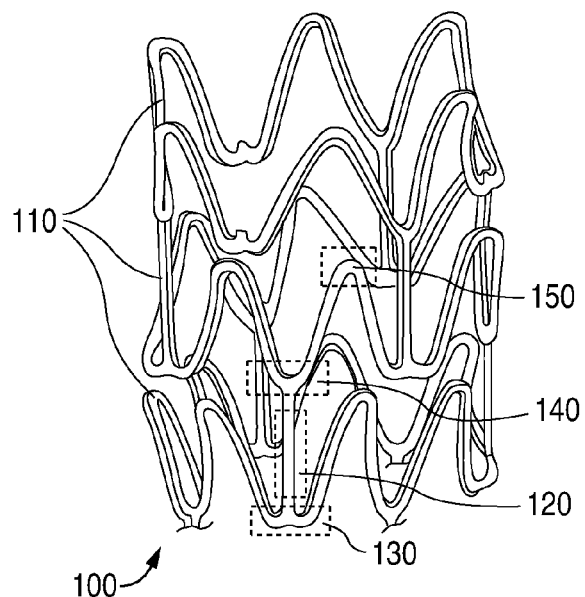
FIG. 1 depicts a stent.

In particular, a stent can have a scaffolding or a substrate that includes a pattern of a plurality of interconnecting structural elements or struts. FIG. 1 depicts an example of a view of a stent 100. Stent 100 may be formed from a tube (not shown). Stent 100 includes a pattern of structural elements 110, which can take on a variety of patterns. The structural pattern of the device can be of virtually any design. The embodiments disclosed herein are not limited to stents or to the stent pattern illustrated in FIG. 1. The embodiments are easily applicable to other patterns and other devices. Structural elements can include, but are not limited to, any element that makes up the structure of the device such as a strut, wire, or filament. The variations in the structure of patterns are virtually unlimited.

Implantable medical devices can be formed from a construct such as a tube, sheet, or other shape or form. A polymer construct, for instance, may be formed by methods such as extrusion or injection molding. A stent such as stent 100 may be fabricated from a polymeric tube or a sheet by rolling and bonding the sheet to form a tube. A stent pattern may be formed on a polymer tube by laser cutting a pattern on the tube. Representative examples of lasers that may be used include, but are not limited to, excimer, carbon dioxide, and YAG. In other embodiments, chemical etching may be used to form a pattern on a tube.

The geometry or shape of an implantable medical device may vary throughout its structure to allow radial expansion and compression. A pattern may include portions of structural elements or struts that are straight or relatively straight, an example being a portion 120. In addition, patterns may include structural elements or struts that include bending elements such as portions 130, 140, and 150. Bending elements bend inward when a stent is crimped and outward when a stent is radially expanded. After deployment, a stent is under static and cyclic compressive loads from the vessel walls. Thus, the curved portions of the bending elements are subjected to relatively high stress and strain during use.

A problem with some biodegradable polymers that have appropriate strength and stiffness for stent applications, such as poly(L-lactide) (PLLA), is that the degradation rate is relatively slow and results in a degradation time of a stent outside of a desired range. Degradation time refers to the time for an implantable medical device to substantially or completely erode away from an implant site. It is generally desirable for a stent to disintegrate and disappear from the region of implantation once treatment is completed. For stents made from a biodegradable polymer, the stent is intended to remain in the body for a duration of time until its intended function of, for example, maintaining vascular patency and/or drug delivery is accomplished. The duration of a treatment period depends on the bodily disorder that is being treated. For illustrative purposes only, the duration can be up to a month, three months, six months, twelve months, eighteen months, or two years.

In general, the initial stage of the degradation of degradable polymer is the decrease or loss in molecular weight due to hydrolysis reactions. The loss in molecular weight causes a loss in mechanical properties which is then followed by mass loss. After a biodegradable implant has lost mechanical properties, such as strength, it is desirable for mass loss to proceed rapidly in order for the implant to be eliminated from the body as quickly as possible.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind.

The degradation time of a slow eroding polymer can be decreased by increasing the degradation rate. The degradation rate may be characterized by, for example, the half-life of a polymer. The "half-life" of a degrading polymer refers to the length of time for the molecular weight of the polymer to fall to one half of its original value. See e.g., J. C. Middleton and A. J. Tipton, Biomaterials, Vol. 21 (23) (2000) pp. 2335-2346.

Several mechanisms may be relied upon for erosion and disintegration of implantable devices which include, but are not limited to, mechanical, chemical breakdown, and dissolution. In particular, degradation of polymers involves chemical breakdown involving enzymatic and/or hydrolytic cleavage of a device material due to exposure to bodily fluids such as blood. Hydrolysis is a chemical process in which a molecule is cleaved into two parts by the addition of a molecule of water. Consequently, the degree of degradation in the bulk of a polymer is strongly dependent on the concentration of water in a polymer and the diffusion rate of water into the polymer.

As discussed above, some biodegradable polymers, such as PLLA, have a degradation rate that is slow and results in a degradation time of a stent outside of a desired range. Increasing the equilibrium content of moisture in a biodegradable polymer that degrades by hydrolysis can increase the degradation rate of a polymer and decrease the degradation time of a stent fabricated from the polymer.

Figure 2:
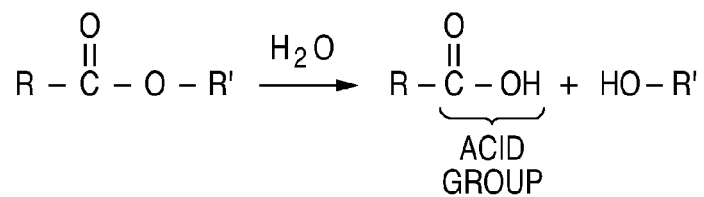
FIG. 2 depicts a hydrolysis reaction of an ester linkage in a polymer to an acid group and an alcohol group.

The degradation rate of some biodegradable polymers, particularly hydrolytically degradable polymers, is a function of the pH of the local environment of the polymer. In particular, the degradation rate tends to increase as the pH decreases. For example, as shown in FIG. 2, a biodegradable polymer can include ester linkages that can degrade through addition of water into a segment having an acid end group and another segment that is an alcohol. The rate of the hydrolysis reaction in FIG. 2 increases as the pH of its local environment decreases. Furthermore, acid groups tend to be hydrophilic which increases the water uptake, further increasing the hydrolysis reactions.

Certain embodiments of the present invention include fabricating a stent from a biodegradable polymer in which the degradation rate has been enhanced or increased by altering the chemistry of the polymer. In some embodiments, the chemistry can be altered by increasing a concentration of acidic groups in the polymer. Increasing the concentration of acidic groups in the polymer tends to decrease the local pH of the polymer upon exposure to bodily fluid, which increases the degradation rate of the polymer.

In some embodiments, a method of increasing the degradation rate of a biodegradable polymer and decreasing the degradation time of a device fabricated from the polymer is to use an acid containing group as an initiator during the synthesis of biodegradable polymer. For example, an acid containing alcohol, R—OH, can be used to initiate polymerization of at least one type of monomer, where R is an acid group such as carboxylic acid. The R—OH group can be used as an initiator in a polymerization reaction in the presence of a monomer and stannous octoate at an elevated temperature to form a polymer with an acid end group, R—[X]n-OH. [X]n is a chain of repeat units of monomers. [X]n can include hydrolytically degradable monomers, for example, DL-lactide, L-lactide, glycolide, or any combination thereof.

Figure 3:
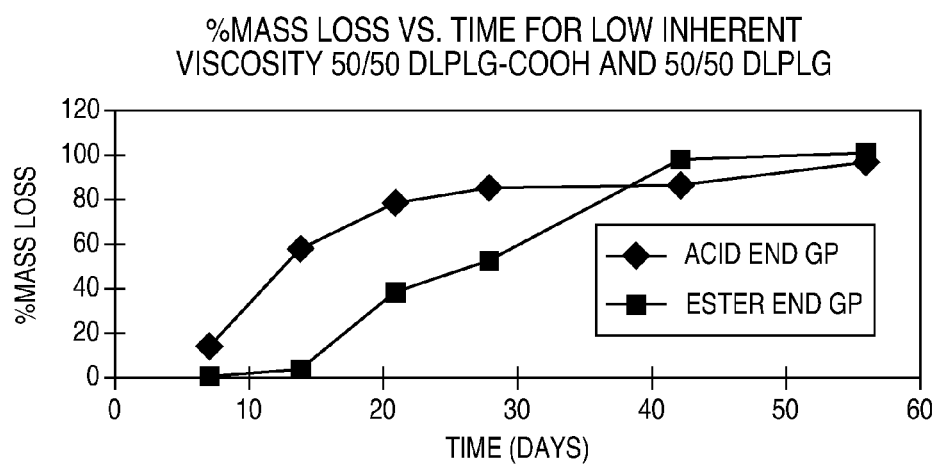
FIG. 3 depicts the mass loss as a function of time for two polymers.

In an exemplary embodiment, a 50:50 copolymer of DL-lactide and glycolide was synthesized by using a carboxylic acid initiator, poly(DL-lactide-co-glycolide)-COOH. The mass loss as a function of time was determined for synthesized polymer having the acid group and a polymer terminated by ester end groups with no acid end group. FIG. 3 depicts the mass loss as a function of time for the two polymers. The time required for 50% mass loss is 12 days for the acid end group polymer compared to 25 days for the ester end group polymer. Thus, the half-life of the polymer with the acid end groups is less than half that of the polymer with the ester end groups.

In general, the increase in the degradation rate is a function of the molecular weight of the polymer. A low molecular weight polymer has a relatively high number of chain ends per unit mass. As a result, it is expected that increasing acid group concentration in a polymer with a low molecular weight will have a greater impact on the degradation rate than a polymer with a high molecular weight, since the high molecular weight polymer has a lower density of chain ends.

As indicated above, an implantable medical device, such as a stents, can be fabricated from biodegradable polymers with acid end groups. The degradation rate of a biodegradable polymer and a degradation time of a device fabricated from the biodegradable polymer can be tailored by controlling the number density of acid end groups. The number density can be controlled, for example, by having the acid group initiator as a limiting reactant to limit the number of acid groups in the synthesized polymer. Alternatively, the polymers with acid end groups can be blended with polymers without acid end groups to obtain a desired degradation rate.

In some embodiments, an implantable medical device such as a stent can be fabricated from a biodegradable polymer having acid end groups at each end of a polymer chain. Some embodiments of fabricating the polymer stent can include synthesizing a biodegradable polymer with a polymer chain with acidic groups at each end of the chain. The polymer chain between the acidic groups includes hydrolytically degradable functional groups. For example, the synthesized polymer can have the form R—[X]n-R'. R and R' can correspond to acidic groups such as a carboxylic acid group ($C(CH_3)COOH$). [X]n can correspond to a chain of hydrolytically degradable functional groups, for example, functional groups having include ester linkages. The functional groups can include, for example, lactide, glycolide, or caprolactone.

A method of synthesizing a biodegradable polymer with a polymer chain with acidic groups at each end of the chain can include first synthesizing an intermediate polymer with one acid end group. Specifically, the intermediate polymer can include a chain with a plurality of hydrolytically degradable functional groups and an acidic end group at one end of the chain. The intermediate polymer can be synthesized by initiating polymerization of the functional groups with an acid containing alcohol. Thus, the intermediate polymer can have the form R—[X]n-OH, where R is an acid end group and [X]n is a plurality of degradable functional groups. X can "n" repeat units of the same functional group or a copolymer including two or more functional groups in any number in any proportion.

After the polymerization yields an intermediate polymer with a sufficient number of repeat units, n, an end-product polymer can be formed from the intermediate polymer having acid groups at both ends of the polymer chain. The end-product polymer can take the form R—X—R', where, R' is the same or different acid group as R.

Figure 4A:
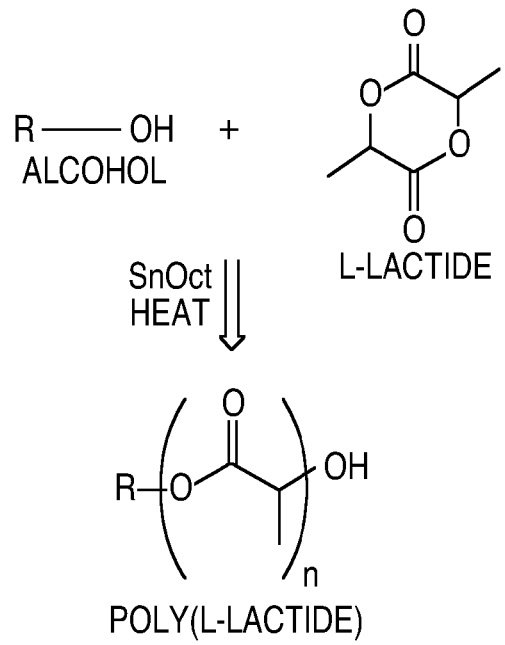
FIG. 4A depicts an exemplary embodiment of synthesizing PLLA with an acid end group.

FIG. 4A depicts an exemplary embodiment of synthesizing the intermediate polymer having one acid end group. As shown, a polymerization reaction of lactide monomers is initiated with an acid containing alcohol, R—OH. In this example, R is a carboxylic acid, $C(CH_3)COOH$. The reaction occurs in the presence of a stannous octoate catalyst at an elevated temperature. A typical temperature for this reaction would be 160° C., although it is well known to those skilled in the art that a range of temperatures from 110° C. to over 200° C. can be employed in this reaction. The intermediate polymer formed is PLLA with an acid end group, R, having "n" lactide repeat units.

Figure 4B:
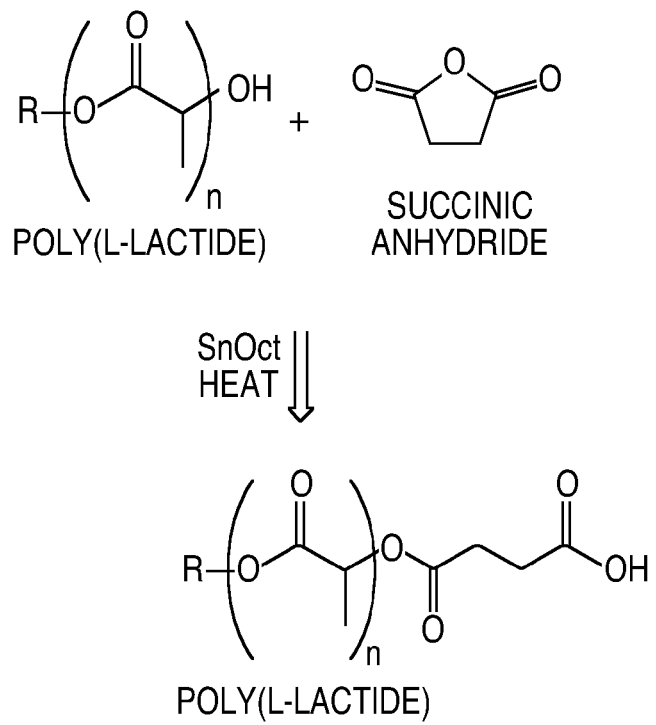
FIG. 4B depicts the exemplary embodiment of the synthesis of PLLA with two acid end groups from the PLLA synthesized in FIG. 4A.

FIG. 4B depicts an exemplary embodiment of the synthesis of an end-product polymer from the PLLA polymer from FIG. 4A. The PLLA reacts with succinic anhydride in the presence of a stannous octoate catalyst at an elevated temperature to form a PLLA with end groups at each of the polymer. The succinic anhydride end-caps the PLLA with an acid group.

In other embodiments, the concentration of acidic groups in a biodegradable polymer can be increased by incorporating polymer structures that have a greater number of chain ends to which acid groups can be added. For example, the concentration of acid end groups can be increased by incorporating branched polymer structures for use in fabricating stents.

In general, branched polymers are formed when there are "side chains" attached to a main chain. Examples of branched polymer structures include star-shaped, dendritic, or comb structures.

A star-shaped polymer refers to a polymer having at least three chains or arms radiating outward from a center. A dendritic polymer is a branched polymer resembling a tree-like structure. A comb structure corresponds to a linear polymer segment or backbone having a plurality of side chains extending outward from a position along the linear segment. In the embodiments described herein, the various polymer structures include a plurality of hydrolytically degradable functional groups.

Figure 5A:
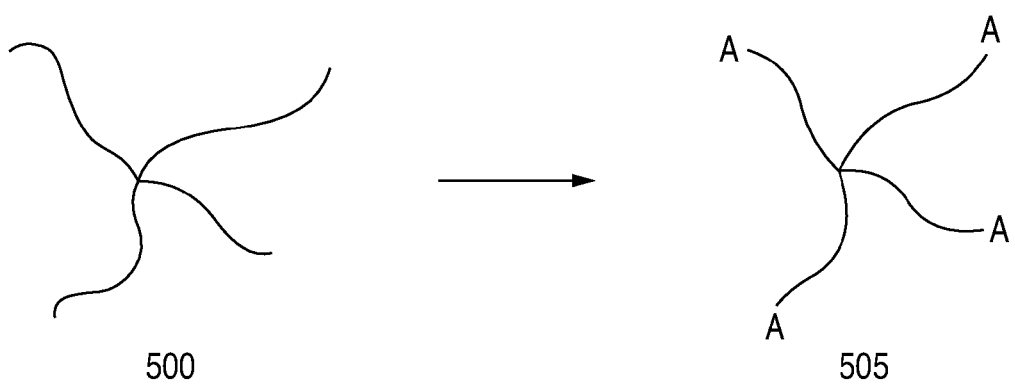
FIGS. 5A-C depict diagrams of polymers having star-shaped, dendritic, and comb structures.
Figure 5B:
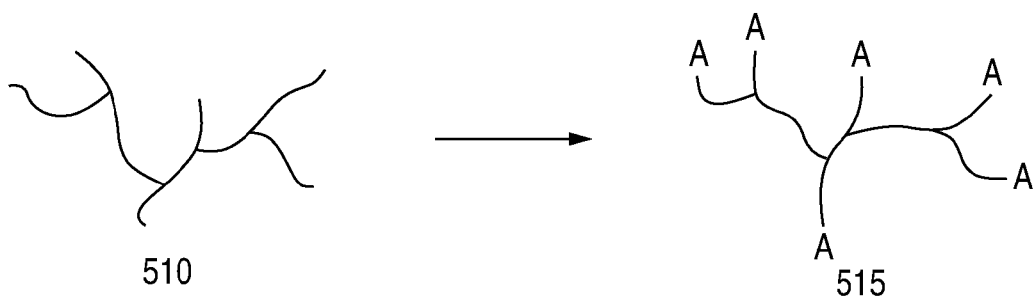
Figure 5C:
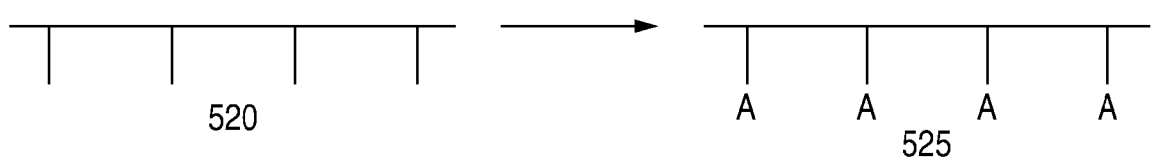

FIGS. 5A-C depict diagrams of polymers having star-shaped 500, dendritic 510, and comb 520 structures in which the polymer chains are represented as lines. The lines correspond to a plurality of hydrolytically degradable functional groups. Acid end groups can be added to star-shaped polymer 500 in FIG. 5A to form star-shaped polymer 505, where "A" represents an acid end group. Acid end groups can be added to dendritic polymer 510 in FIG. 5B to form dendritic polymer 515. Acid end groups can be added to comb-shaped polymer 520 in FIG. 5B to form comb-shaped polymer 525.

Synthesis of lactide-based polymers having star-shaped, dendritic, or comb structures with acid end groups involves first obtaining or synthesizing polymers with the respective structures having, for example, ester end groups. Polymers with acid end groups can then be synthesized by reacting the polymers with the ester end groups with succinic acid, as described above.

Figure 6:
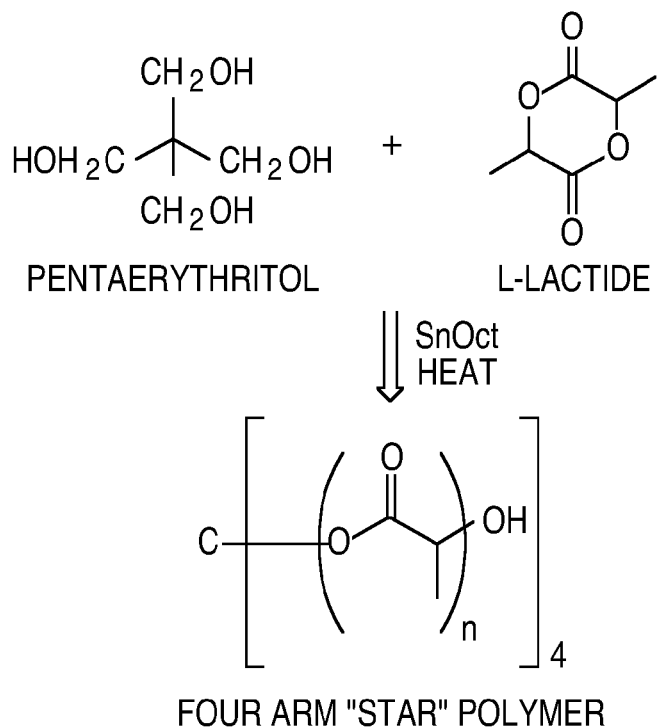
FIG. 6 depicts a synthesis of a PLLA star-shaped polymer with four arms.

In an exemplary embodiment, a star-shaped polymer can be synthesized according the scheme depicted in FIG. 6. In FIG. 6, pentaerythritol is reacted with L-lactide monomer in the presence of a stannous octoate catalyst at an elevated temperature. As shown, a four arm PLLA polymer with ester end groups is formed. The four arm PLLA polymer can be reacted with succinic acid as described in reference to FIG. 4B to add acid end groups at the end of the arms of the four arm PLLA.

Figure 7:
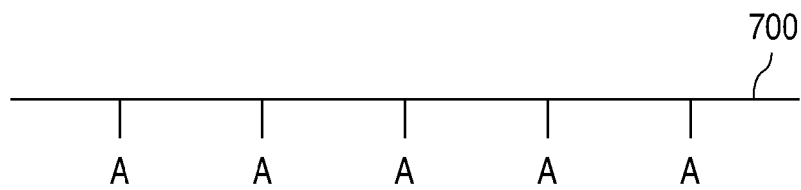
FIG. 7 depicts a polymer backbone with pendant acid groups.

In additional embodiments, a degradation rate of a hydrolytically degradable polymer can be enhanced by including acid side groups as pendant groups along a polymer backbone. FIG. 7 depicts a diagram of a polymer with the backbone 700 represented as a lines. The lines correspond to a plurality of hydrolytically degradable functional groups. Polymer backbone 700 includes acid side groups, "A", as pendant groups along backbone 700.

Figure 8A:
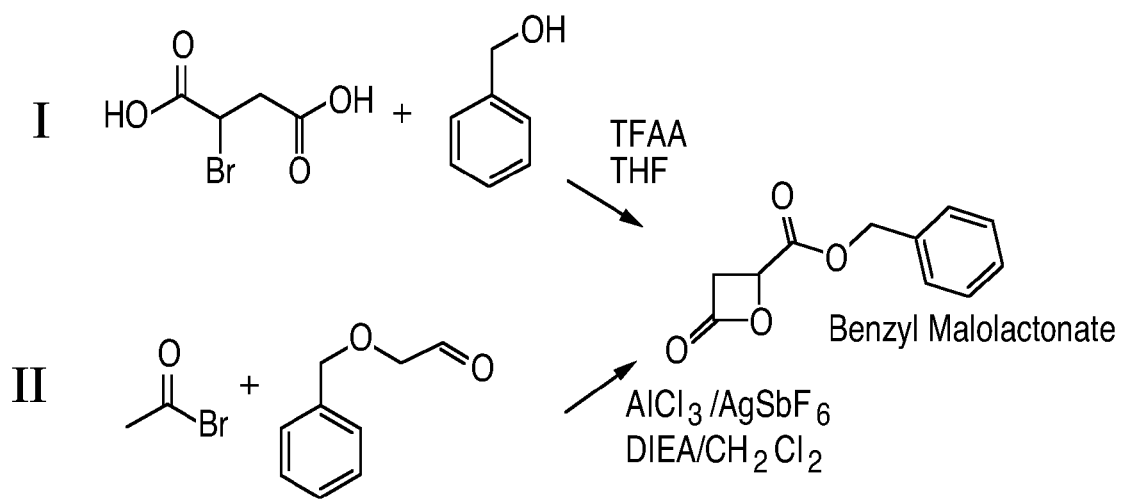
FIGS. 8A-C depict a synthesis route for PLLA containing pendant acid groups.
Figure 8B:
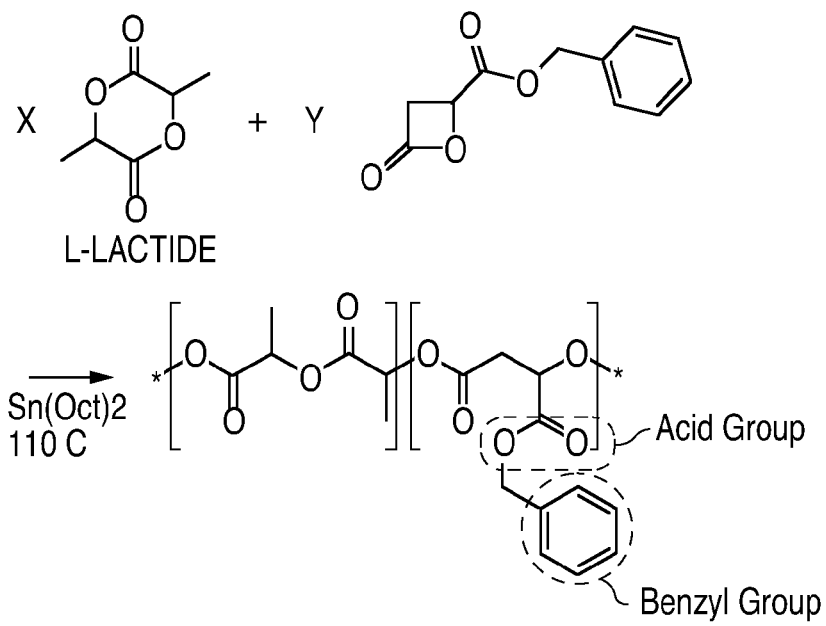
Figure 8C:
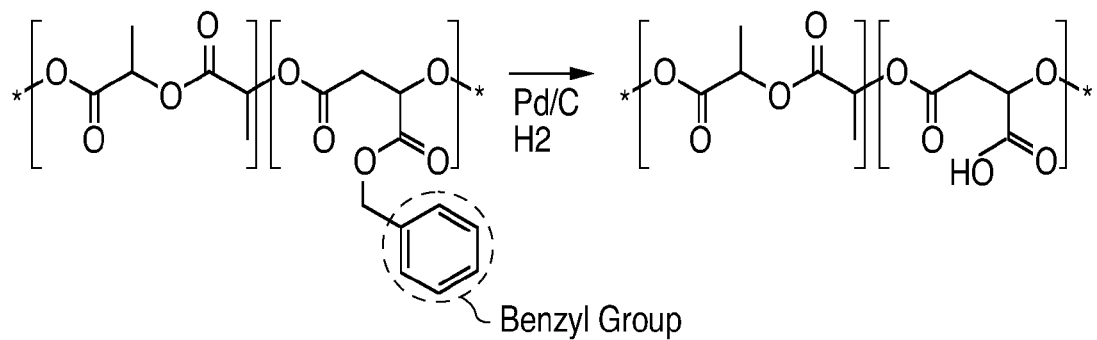

A synthesis scheme for PLLA containing pendant acid groups is shown in FIGS. 8A-C. Biomaterials, 25 (2004) 5239-5247. The first step of the route is to synthesize benzoyl malactonate. FIG. 8A depicts two different ways to synthesize benzyl malactonate.

FIG. 8B depicts the second step in the synthesis route in which benzyl malactonate is copolymerized with other lactones and lactides using stannous octoate as a catalyst. The copolymerization can also be performed enzymatically. Materials with high molecular widths and narrow polydispersities can be obtained. The benzyl group acts as a protecting group for the acid group during the synthesis scheme. The protecting group prevents the acid group causing or accelerating premature hydrolytic degradation of the degradable polymer that is formed in the following step. In general, a protecting group refers to a group that is used to protect a functional group from causing or participating in unwanted reactions. The protecting group can be removed at a later time to reveal the original functional group.

The third step in the synthesis route is the removal of the benzyl group from the copolymerization of benzyl malactonate depicted in FIG. 8B. FIG. 8C depicts removal of the benzyl group by hydrogenation to yield a carboxylic acid functionality on the degradable lactide backbone. The group can be used to tailor the degradation properties of the material since degradation of lactides is accelerated in an acidic environment. The carboxylic acid group can also be used to attach moieties on to the backbone. The removal of the benzyl ester is easily done by hydrogenation in high yield, and the only side product, benzyl alcohol, can easily be boiled off or removed by a dissolution/precipitation process.

Other routes for the synthesis of polymers containing pendant acid groups are know to those skilled in the art. This route is shown for illustrative purposes only.

It is believed that the pendant acid group may inhibit growth of crystalline domains with a polymer. If desired, this can be avoided by grouping the acid functionalities in one part of the polymer chain. This would yield a block polymer, with the acid moieties grouped in a block. One method to achieve this block structure would be to add the benzyl malolactonate at the final stages of the synthesis of the polymer. This would concentrate the acid moieties at the end of the polymer chain.

Accelerating degradation by increasing the concentration of acid groups in a biodegradable polymer through end groups is limited by the number density of end groups in a polymer. Additionally, the enhancement of degradation can be limited by the strength of the acid group. The "strength" of an acid is measured by the value of its dissociation constant or the ability of the acid to donate protons. The strength of an acid has to do with the percentage of the initial number of acid molecules that are ionized. If a higher percentage of the original acid molecules are ionized, and therefore, donated as hydrated protons (hydronium ions) then the acid will be stronger. Thus, degradation rate can be enhanced further by pendant acid groups on a polymer chain as well as stronger acid groups.

Further embodiments of a biodegradable polymer for use in stents include a block polymer having a hydrolytically degradable block and at least one acidic polymer block including a plurality of pendant acid groups. Due to degradation of hydrolytically degradable block, the acidic polymer block can be cleaved from the biodegradable block upon exposure to bodily fluids. Therefore, after implantation, the degradable block hydrolytically degrades allowing acidic polymer blocks to separate from the degradable block. The cleaved or separated acidic polymer blocks can be transported away from the tissue and excreted by the kidney.

For example, the block copolymer can have the general formula: HO—[X]n-[Y]m, where X corresponds to hydrolytically degradable functional groups and Y corresponds to functional groups of the acidic polymer. Since the acidic block can be of any desired length, the concentration of acid groups can be much higher than that obtained by addition of acid end groups.

In one exemplary embodiment, the hydrolytically degradable block is PLLA. An acidic polymer block in this embodiment can include sulfonic acids including, but not limited to, polystyrene sulfonate or poly(2-acrylamido-2-methylpropanesulfonic acid). Sulfonic acids are stronger than carboxylic acids, and thus can accelerate hydrolysis reactions more effectively.

In some embodiments, the block copolymer can be used in the fabrication of a stent. The stent can be composed in whole or in part of the block polymer. In one embodiment, a biodegradable polymer can be blended with the block copolymer to increase the degradation rate. The amount of blended block copolymer can be adjusted to obtain a desired degradation rate or degradation time of a stent. In exemplary embodiments, the block copolymer can be less than 60 wt %, 40 wt %, 25 wt %, 10 wt %, or less than 5 wt % of a blend. For example, PLLA can be blended with a PLLA-polystyrene sulfonate block copolymer.

In some embodiments, a stent can be fabricated from a blend in which the acidic polymer block of the block copolymer can phase separate or is immiscible with the hydrolytically degradable polymer of the blend. "Immiscible" refers to the inability of a polymer blend to form a single phase in selected ranges of composition of the blend and in the ranges of temperature and pressure at (1) ambient conditions (1 atm, 15° C. to 30° C.), (2) during processing of the composite and device, and (2) at physiological conditions. For example, the sulfonic acid polymer block can be immiscible with PLLA. The hydrolytically degradable block of the block copolymer, e.g., a PLLA block, may phase separate out from the acidic polymer block into the PLLA. Thus, the blend can have two phases. One phase can includes at least the acidic polymer block and the other phase includes the hydrolytically degradable polymer and can also include the hydrolytically degradable block. The miscibility depends on the specific functional groups of the sulfonic acid polymer.

Since hydrolytically degradable polymers as PLLA are very sensitive to acid groups in solution, it is desirable to use appropriate chemistry to allow the synthesis of these block copolymers. An exemplary embodiment of the fabrication the block copolymer can include three steps. In the first step a polymerization reaction forms an acidic copolymer having a protected acid group. The protecting group prevents the acid group donating a proton which can cause premature hydrolytic degradation of the degradable polymer that is formed in the following step. In the second step, the acidic polymer initiates polymerization of the hydrolytically degradable polymer to form a block copolymer with the protected acid group. In the third step, the protecting group can be removed from the block copolymer.

Figure 9A:
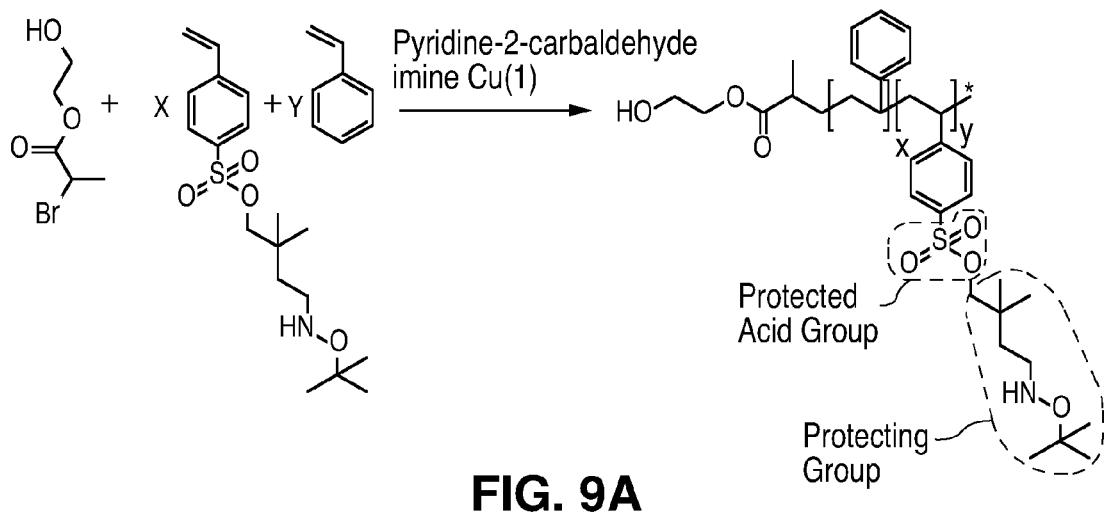
FIGS. 9A-C depict a synthesis scheme for PLLA-polystyrene sulfonate block copolymer.
Figure 9B:
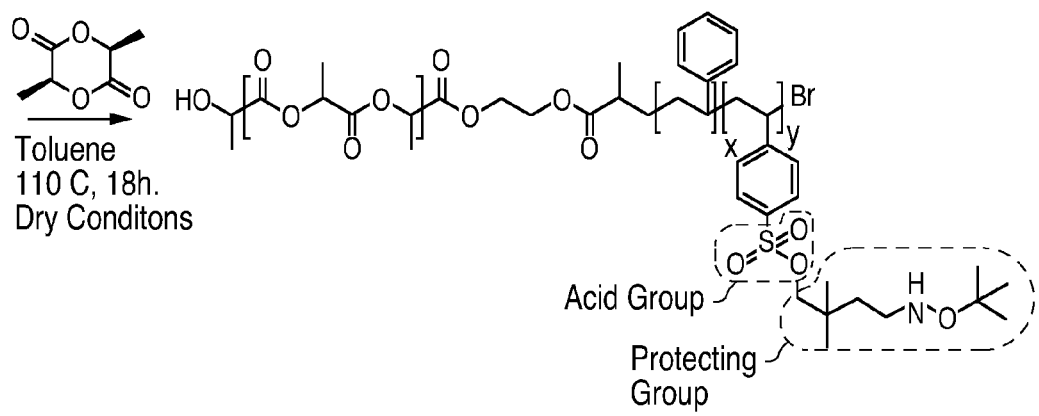
Figure 9C:
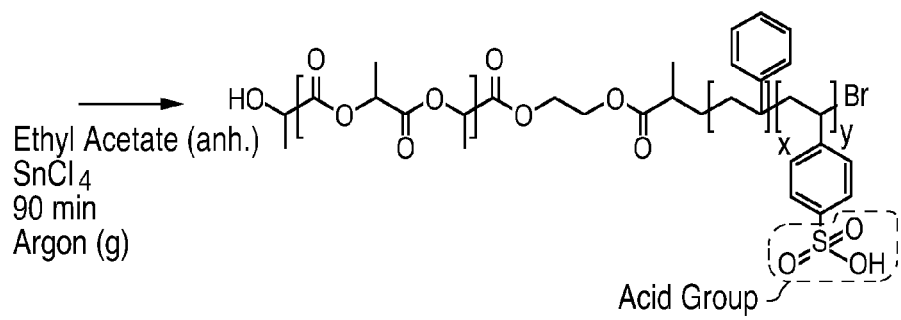

FIGS. 9A-C depict an exemplary synthesis scheme for PLLA-polystyrene sulfonate block copolymer. The first step in FIG. 9A shows the synthesis of a poly(styrene-r-styrene sulfonate) copolymer which will be subsequently used to initiate polymerization of PLLA in the second step. Poly(styrene-r-styrene sulfonate) is formed from a 2-hydrohyethyl-2'-methyl-2'-bromopropionate initiator, and two styrene based monomers in the presence of pyridine-2-carbaldehyde imine Cu(I) catalyst. The poly(styrene-r-styrene sulfonate) copolymer formed has a hydroxyl end group, a protected sulfonic acid group, and a protecting group. The exemplary protecting group is N-BOC-4-amino-2,2'-dimethylbutyl (BOC). Other protecting groups are well known to those skilled in the art. The protecting group prevents the acid group causing or accelerating premature hydrolytic degradation of PLLA when it is formed in the second step.

FIG. 9B depicts the second step of the synthesis scheme for poly(L-lactide)-polystyrene sulfonate block copolymer. The poly(styrene-r-styrene sulfonate) copolymer formed in the first step initiates the polymerization of lactide monomer. The polymerization is performed in toluene at 110° C. under dry conditions.

FIG. 9C depicts the final step of the synthesis which is the removal of the BOC protecting group. In this step, it is desirable for the solution to not contain water. If water is present, the unprotected sulfonic acid group can rapidly degrade the PLLA block. The reaction is performed in the presence of anhydrous ethyl acetate and a stannous chloride catalyst.

In an alternative embodiment, acrylate monomers, such as hydroxyethylmethacrylate, methyl methacrylate, or 2-(dimethylamino)ethyl acrylate can be polymerized in the first step. The same initiator, (2-hydrohyethyl-2'-methyl-2'-bromopropionate), and catalyst, (pyridine-2-carbaldehyde imine Cu(II)), can be used. The acrylate monomers are used in place of the styrene based monomers in the first step of the synthesis.

In an embodiment, the block copolymer with the unprotected sulfonic acid groups can be used in the fabrication of a stent. For example, the PLLA-polystyrene sulfonate block copolymer formed in the final step can be used in the fabrication of a stent.

In some embodiments, a radiation sensitive protecting group can be used in the synthesis of the acidic polymer, for example in the first step in FIG. 9A. A radiation sensitive group refers to a group that can undergo chain scission when exposed to a selected type of radiation. Various kinds of radiation can be used to cause chain scission, for example, ultraviolet (UV), electron beam (e-beam), ion beam, x-ray, laser, and gamma. E-beam can cause chain scission with exposures at least between 5 kGy and 10 kGy. Ion beams can cause chain scission in the range of $4 \times 10^{-14}$ to $1.2 \times 10^{-14}$ ions/cm$^2$. An IR-laser is expected to cause chain scission with a pulse power of 1 W/cm$^2$ for 0.1 seconds.

In some embodiments, a stent can be fabricated from the block copolymer with a radiation sensitive protecting group. Thus, the removal of the acid protecting group in FIG. 9C is not performed. The protecting group provides the advantage of accelerated degradation due to the acid groups, with reduced or eliminated premature degradation. For example, the presence of the acid protecting group can reduce or prevent degradation of the stent between fabrication the removal of the protecting group. The protecting group can extend the shelf life of the stent, particularly if the stent is exposed to moisture during storage.

Furthermore, the accelerated degradation can be triggered in the stent by exposing the stent to radiation. The stent can be exposed to radiation at any time between fabrication of the stent to any time after implantation of the stent in a vessel. In one embodiment, the accelerated degradation can be triggered upon implantation by irradiating the implanted stent with a UV catheter. The accelerated degradation of the stent would, therefore, start when implanted. In another embodiment, the accelerated degradation may be triggered once the healing of the stented vessel has been deemed sufficient, i.e., once a non-invasive imaging method shows that the vessel no longer needs mechanical support. This would allow tailoring of the lifespan of the polymeric stent to the actual healing of the vessel.

In other embodiments, a polymer including acid groups for use in fabricating a stent can be a copolymer. The copolymer can be composed of a hydrolytically degradable functional group and an acidic functional group with a pendant acid group. For example, the copolymer can have lactide groups and sulfonic acid groups. The copolymer can have the degradable and acidic functional groups in any order and any proportion. The ratio of degradable to acidic functional groups can be adjusted to tailor the degradation rate or degradation time of the stent. Thus, the degradation rate or degradation time of a stent can be tuned to desired values. As the degradable functional groups degrade, the acidic functional groups can be released and eliminated by the body. A stent can be made in whole or in part of the copolymer. In one embodiment, the copolymer can be an additive to a biodegradable polymer to tune the degradation rate or degradation time of the stent.

In some embodiments, an acidic polymer can be blended with a hydrolytically degradable polymer to tune or adjust the degradation rate of a stent. For example, the poly(styrene-r-styrene sulfonate) copolymer, with or without the protecting group, can be blended with PLLA.

Further embodiments of enhancing the degradation rate of biodegradable polymer stent can include incorporating polymeric structures that reduce or inhibit formation of crystalline domains in the biodegradable polymer. Many biodegradable polymers, such as PLLA, suitable for use in stents are semicrystalline polymers. The microstructure of such polymers can include crystalline domains dispersed within an amorphous domain. The degradation rate of crystalline domains within a semicrystalline polymer, such as PLLA, tends to be much slower than the degradation rate of amorphous regions of the polymer. Crystalline regions tend to be more tightly packed which inhibits uptake of moisture. Thus, decreasing crystallinity and the inhibiting formation crystalline domains tends to increase moisture uptake and enhance degradation.

As indicated above, after a biodegradable implant has lost mechanical properties, such as strength, it is desirable for mass loss to proceed rapidly in order for the implant to be eliminated from the body as quickly as possible. Some embodiments of a stent composed of a semicrystalline degradable polymer can include incorporating molecular species that reduce or eliminate microcrystalline formation at the latter stages of degradation. For semicrystalline polymers, there tends to be an increase in crystallinity during degradation. The increase in crystallinity tends to slow the rate of degradation. Microcrystalline formation can be reduced or eliminated by incorporating branched polymer structures into a biodegradable polymer. As indicated above, branched polymer structures can includes star-shaped and dendritic structures. Such structures tend to inhibit formation of crystalline domains.

In some embodiments, a structural element can be composed in whole or in part of a hydrolytically degradable star-shaped or dendritic polymer such as PLLA. The structural element can be composed entirely of one type of branched structure, e.g., star-shaped or dendritic. Alternatively, the structural element can include a mixture of two or more types of structures, e.g., star-shaped and dendritic. In some embodiment, the branched polymer structures can have acid end groups, as described above.

In other embodiments, the structural element can be composed of a blend including a linear or unbranched hydrolytically degradable polymer and a branched polymer such as a star-shaped or dendritic polymer. In another embodiment, the blend can include a linear polymer and a mixture of more than one type of branched structures.

In some embodiments, the branched polymers can be a derivative of the linear polymer, being composed of the same hydrolytically functional groups. For example, the blend can include linear PLLA and a star-shaped PLLA structure. In alternative embodiments, the branched polymer structure in the blend can include functional groups different from the linear biodegradable polymer.

Branched polymer structures can be synthesized in a number of ways. For example, a synthetic scheme for a four arm star-shaped PLLA is depicted in FIG. 6. Other synthesis schemes have branched PLLA have been disclosed in the literature, for example, Tadeusz Biela et al., J. of Pol. Sci. Part A: Polymer Chemistry, Volume 43, Issue 23, Pages 6116-6133, "Star-shaped poly(L-lactide)s with variable numbers of hydroxyl groups at polyester arms chain-ends and directly attached to the star-shaped core—Controlled synthesis and characterization" and Youliang Zhao et al., Chem. Mater., 15 (14), 2836-2843, 2003, "Synthesis and Characterization of Star-Shaped Poly(L-lactide)s Initiated with Hydroxyl-Terminated Poly(Amidoamine) (PAMAM-OH) Dendrimers."

Various parameters of the branched polymer and the blends can influence, and thus, can be used to tune the degree of crystallization, and thus, degradation rate. In blends, the ratio of the linear and the branched polymer structures can be adjusted to obtain a desired degradation rate. Additionally, the structure of the branched polymers can affect the crystallization and degradation rate, for example, the number of arms, degree of branching, and the molecular weight. The effects of molecular weight and number of arms on the thermal properties and hydrolytic degradation of star-shaped polylactides have been investigated. Ibid.

Further embodiments of enhancing the degradation rate of a biodegradable polymer stent include incorporating a hydrophilic component into the biodegradable polymer to increase the equilibrium content of moisture in the stent. The presence of the hydrophilic component can increase the equilibrium moisture content in the stent. The degradation rate of a hydrolytically biodegradable polymer such as PLLA is accelerated by increasing the equilibrium moisture content of the polymer.

In some embodiments, the hydrophilic component can be an acid group such as carboxylic acid, as described above. In other embodiments, the hydrophilic component can be a hydrophilic polymer such as polyethylene glycol (PEG) or poly(vinyl alcohol) (PVA). Various embodiments of incorporating hydrophilic content into a stent are disclosed herein. In each embodiment, the hydrophilic content can be adjusted or varied, allowing variation of the degradation rate.

In certain embodiments, a structural element of a stent can include a blend of a hydrolytically degradable polymer and one or more types of hydrophilic polymers. The degree of hydrophilic content of the polymer can be adjusted to obtain a desired degradation rate of the polymer and degradation time of the structural element. The degree of hydrophilicity can be controlled by the overall content or weight fraction of the hydrophilic component, for example, ethylene glycol or vinyl alcohol in the polymer. The content can be increased by increasing the amount of hydrophilic polymer or increasing the molecular weight of hydrophilic polymer. The weight fraction of hydrophilic groups can be less than 50 wt %, 30 wt %, 20 wt %, 10 wt % or more narrowly, less than 10 wt %.

Figure 10:
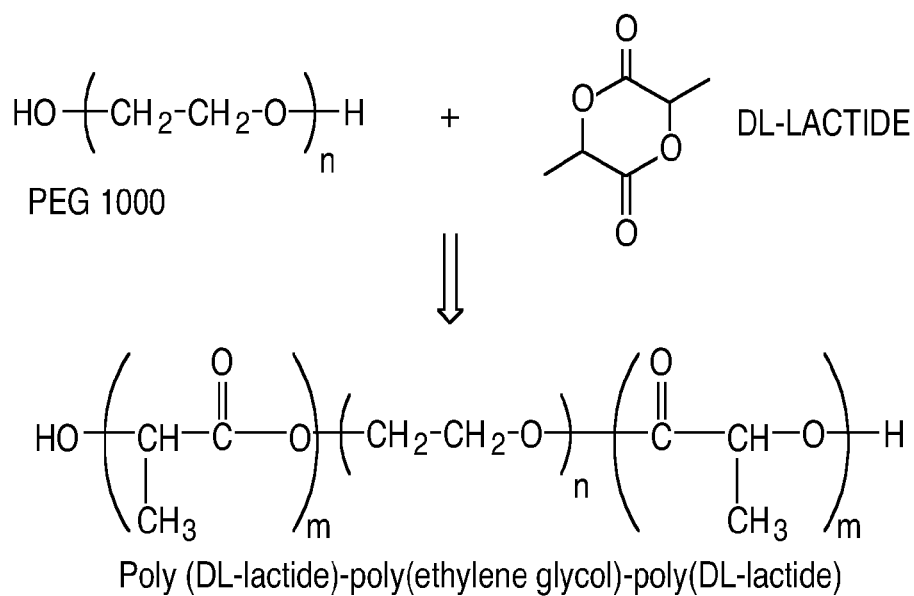
FIG. 10 depicts an exemplary synthesis scheme of a PLLA-PEG block copolymer from PEG and lactide monomer.

In another embodiment, a structural element of a stent can include a block copolymer including a hydrolytically degradable polymer block and a hydrophilic polymer block. The synthesis of such block copolymers is known in the art. For example, block copolymers of PLLA, PGA, and PLGA with PEG have been disclosed. Drug Delivery Technology, July/August 2003, Vol. 3 No. 5. For example, the block copolymer can be PLLA-b-PEG-b-PLLA. FIG. 10 depicts an exemplary synthesis scheme of a PLLA-PEG block copolymer from PEG and lactide monomer. The reaction is carried out at 160° C. in the presence of stannous octanoate. The relative content of the hydrophilic component in the polymer can be adjusted by varying the number of hydrophilic blocks and the molecular weight of the hydrophilic blocks.

In further embodiments, a structural element of a stent can include a blend of a hydrolytically degradable polymer and a block copolymer including the hydrolytically degradable polymer and a hydrophilic polymer. As above, the relative content of the hydrophilic component can be adjusted by varying the number of hydrophilic blocks and the molecular weight of the hydrophilic blocks. In addition, the relative content of the hydrophilic component can be adjusted by varying the relative amount of the hydrolytically degradable polymer and the block copolymer. Thus, the degradable polymer/block copolymer blend allows the greatest degree of freedom in varying the hydrophilic content, and thus, the degradation rate of the stent.

In certain embodiments, a structural element including hydrophilic polymers can be designed to have a spatially nonuniform distribution of hydrophilic content. As a result, a nonuniform distribution of moisture content can be established in the structural element upon exposure to bodily fluids. The gradient or nonuniformity in the moisture distribution alters and thus allows control over the spatial degradation profile of the structural element. Thus, appropriate selection of a nonuniform distribution of hydrophilic content in a structural element can provide a desired degradation profile.

In one embodiment, there can be a gradient in hydrophilic content between an inner region and an exterior or surface region of the structural element. In an embodiment, the hydrophilic content is highest in the center or inner region and decreases to the exterior region. The degradation rate is enhanced at the center of the structural element, while at the same time allowing the rapid clearance of degradation products from the interior to the exterior due to the higher diffusivity of the hydrophilic polymer. The hydrophilic content can be varied according to any of the embodiments described above.

Figure 11:
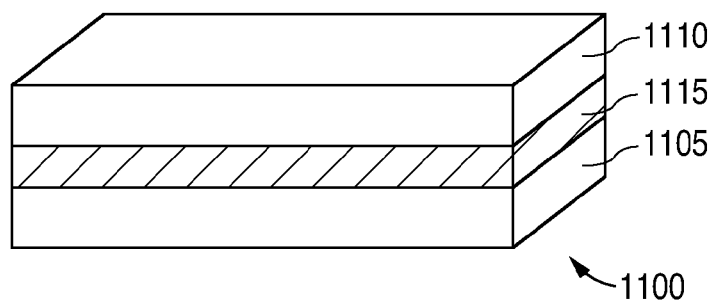
FIG. 11 depicts a portion of a structural element with an abluminal layer and a luminal layer and an inner layer.

FIG. 11 depicts a portion 1100 of a structural element with an abluminal layer 1105 and a luminal layer 1110 and an inner layer 1115. Inner layer 1115 has a higher hydrophilic content than abluminal and luminal layers 1105 and 1110. A stent having the structural element can be formed by coextruding a tube with the layers having different hydrophilic content and then laser cutting the tube to form a stent.

Figure 12:
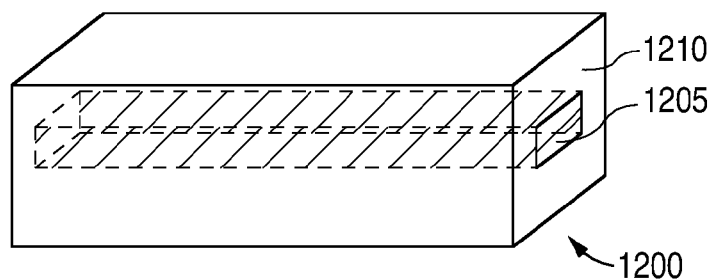
FIG. 12 depicts a portion of a structural element having an inner core region surrounded by an outer region.

FIG. 12 depicts a portion 1200 of a structural element having an inner core region 1205 surrounded by an outer region 1210. Similarly, FIG. 13 depicts a portion 1300 of a cylindrical structural element having an inner core region 1305 surrounded by an outer region 1310. The structural elements of portions 1200 and 1300 can be coextruded filaments. Alternatively, core regions 1205 and 1305 can be a substrate and outer regions 1210 and 1310 can be a coating.

FIG. 14A depicts two hydrophilic content distributions, 1400 and 1405, through a cross-section of a structural element through an interior region and between exterior surface regions. The interior and exterior regions can correspond to inner layer 1115 and luminal layer 1105/abluminal layer 1110 in FIG. 11, inner core region 1205 and outer region 1210 in FIG. 12, or inner core region 1305 and outer region 1310.

The transition in hydrophilic content between regions of differing hydrophilic content can be discontinuous or continuous. A continuous gradient in hydrophilic content can be obtained, for example, by allowing mixing of layers or regions during coextrusion. The steepness of the gradient can be controlled by varying the amount of mixing that is allowed. A discontinuous gradient can be obtained, for example, by not allowing mixing during coextrusion.

Various other distributions of hydrophilic content can be obtained by including additional layers or regions and/or by selecting a desired hydrophilic content in the layers or regions. For example, the distribution of hydrophilic content can increase from one outer region to another or can be biomodal or multimodal. A bimodal distribution can be obtained by having additional layers or regions with alternating hydrophilic content. FIG. 14B depicts a bimodal distribution of hydrophilic content and FIG. 14C depicts a distribution that increases from one outer region to another in a step-function fashion.

Further embodiments of enhancing the degradation rate of a slow eroding biodegradable polymer stent include incorporating a rapidly degrading biodegradable polymer within the slow degrading biodegradable polymer. Some embodiments can include a stent having a structural element fabricated from a polymer blend including a slow degrading hydrolytically degradable polymer and a fast degrading hydrolytically degradable polymer.

In an embodiment, the fast degrading polymer can have a substantially faster degradation rate than the first polymer. In some exemplary embodiments, the fast degrading polymer with a substantially greater degradation rate can have a half life that is less than 70%, 50%, 30%, 20%, 10%, or less than 5% of the half-life of the slow degrading polymer.

In certain embodiments, the degradation products of the fast eroding polymer can be capable of increasing the degradation rate of the slow eroding polymer. Specifically, the degradation products of the hydrolytically degradable polymer tend to acidic and hydrophilic which can accelerate the degradation of the slow degrading hydrolytically degradable polymer.

As discussed above, the rate of a hydrolysis reaction tends to increase as the pH decreases from a physiological range to an acidic range. Thus, the decrease in the pH due to acidic degradation products of the fast degrading polymer can increase the hydrolytic degradation of the slow degrading polymer. In addition, the acidic degradation products are hydrophilic, which increases the uptake of water into the polymer blend. The increased uptake of water also increases the degradation rate since the hydrolysis reaction of the matrix polymer has water as a reactant.

The weight percent of the fast eroding polymer can be varied to control the degradation rate and the degradation time of the stent. The fast eroding polymer can be, for example, less than 40%, 30%, 20% 15%, or more narrowly, less than 5% by weight of the blend. In one embodiment, the weight percent of the fast eroding polymer can be controlled to be low enough so that a stent fabricated from the blend has adequate mechanical properties.

For example, both the fast degrading and slow degrading polymer can include ester linkages that can degrade by hydrolysis through addition of water into a degradation product having an acid group. FIG. 2 depicts a hydrolysis reaction of an ester linkage to an acid group and an alcohol group. The presence of the acid lowers the local pH which increases the hydrolysis reaction of the ester linkage in both the fast and slow eroding polymer. In addition, the acid group produced is hydrophilic which increases water uptake which further increases the rate of the hydrolysis reaction since the reaction is first order in water concentration.

In some embodiments, the fast degrading polymer and the slow degrading polymer can be miscible. "Miscible" refers to the capability of a polymer blend to form a single phase in selected ranges of composition and in the ranges of temperature and pressure at (1) ambient conditions (1 atm, 15° C. to 30° C.), (2) during processing of the blend and device, and (2) at physiological conditions. In one embodiment, the fast and slow degrading polymers can be uniformly mixed, for example, in an extruder. In another embodiment, the fast eroding polymer can be immiscible with the slow eroding polymer.

In some embodiments, the fast eroding polymer can be in the form of particles mixed or dispersed within a slow eroding polymer matrix. In general, the smaller the particles and more uniformly dispersed the particles, the greater the acceleration of the degradation rate of the slow eroding polymer. Various sizes of the particles may be used. For example, the particles can include, but are not limited to, nanoparticles and microparticles. A nanoparticle refers to a particle with a characteristic length (e.g., diameter) in the range of about 1 nm to about 1,000 nm. In some embodiments, the characteristic length of the nanoparticles can be less than 100 nm. In other embodiments, the characteristic length of the nanoparticles can be less than 300 nm, 500 nm, 700 nm, or less than 900 nm. A microparticle refers to a particle with a characteristic length greater than 1,000 nm and less than about 10 microns. Additionally, particles can be of various shapes. For example, the particles can be spherical, oblong, long fibers, or short fibers.

As the particles erode within the polymeric matrix, the porosity of the matrix is increased. The increased porosity increases the diffusion rate of moisture through the polymeric matrix, and thus, the equilibrium moisture content of the polymeric matrix. As a result, the degradation rate of the polymer is increased. The porous structure also increases the transport of degradation products out of the matrix, which also increases the degradation rate of the matrix.

In some embodiments, a mixture of fast eroding polymer particles in a slow eroding polymer can be formed by melt blending particles with a matrix polymer melt. Melt blending can be particularly useful for mixing particles with a melting temperature (Tm) that is above the Tm of the slow eroding matrix polymer. In one embodiment, a method of fabricating an implantable medical device can include mixing a plurality of fast degrading polymer particles with a matrix polymer melt. The fast degrading polymer can be selected so that it has a Tm above the Tm of the slow degrading matrix polymer. The temperature of the slow degrading matrix polymer melt during mixing can be less than the Tm of the particles so that particles do not melt during the mixing. The particles can be mixed with the matrix polymer melt using an extruder or batch processing. The mixture of slow degrading matrix polymer melt and particles can then be forced through a die to form a polymer tube from which a stent can be made.

Representative examples of extruders include, but are not limited to, single screw extruders, intermeshing co-rotating and counter-rotating twin-screw extruders and other multiple screw masticating extruders.

In one embodiment, the particles can be combined with the slow degrading matrix polymer in a powdered or granular form prior to melting of the matrix polymer. The particles and matrix polymer can be mixed using mechanical mixing or stirring such as by agitation of the particles and polymer in a container or a mixer. The agitated mixture can then be heated to a temperature above the Tm of the matrix polymer in an extruder or using batch processing. The mixture can then be cooled to below the Tm of the matrix polymer. For example, a polymer melt can be cooled by conveying it through a water bath at a selected temperature. Alternatively, the polymer melt may be cooled by a gas at a selected temperature.

Another embodiment of forming a mixture of fast eroding polymer particles with a slow eroding polymer matrix can include melt blending a fast eroding polymer with a slow eroding matrix polymer above the Tm of both the fast eroding polymer and the matrix polymer. To allow for the formation of particles within the matrix polymer, the fast eroding polymer can be immiscible with the matrix polymer. The particles are formed during mixing through microphase separation of the discrete phase particle polymer from a continuous phase matrix polymer.

In one embodiment, a fast degrading polymer can be mixed with a slow degrading matrix polymer, the fast degrading polymer and the slow degrading matrix polymer being above their Tm's. The fast degrading polymer can be added to the slow degrading matrix polymer in a form that facilitates blending of the fast degrading polymer and slow degrading matrix polymer. For example, the fast degrading polymer can be added to the slow degrading matrix polymer in powdered or granular form. The fast degrading polymer melt and the slow degrading matrix polymer melt can be mixed so that the fast degrading polymer forms a plurality of discrete particulate domains having nanoparticle or microparticle characteristic lengths dispersed within the matrix polymer.

In an exemplary embodiment, a rapidly degrading polymer, such as 50/50 poly(DL-lactide-co-glycolide) (DLGLG) can be blended with a slow degrading PLLA. The blend can be approximately 5-15 wt % of 50/50 DLGLG. As described above, the degradation products of 50/50 DLPLG are acidic and hydrophilic. Thus, as the 50/50 DLPLG preferentially erodes it will form acidic degradation products that will serve to enhance the degradation rate of the PLLA. The degradation products are also hydrophilic which will serve to increase the equilibrium level of moisture in the polymer. Both of these mechanisms will increase the degradation rate of any implant manufactured from these materials.

As described above, a biodegradable stent should provide support to a vessel during a clinically relevant time frame, after which the stent is absorbed, leaving behind a healthy blood vessel. During the clinically relevant time frame, the stent performs its intended function of, for example, maintaining vascular patency and/or drug delivery. Ideally, a stent provides mechanical support for the desired time period, and then rapidly, and safely bioabsorbs over a short period of time. Thus, it would be desirable for the stent to degrade slowly during the clinically relevant time frame and degrade faster afterwards.

Certain embodiments of treating a vessel or bodily lumen can include locally treating an implanted a hydrolytically degradable polymer stent, to change its degradation rate. The localized treatment can increase the degradation rate of a stent by increasing or decreasing the pH of bodily fluid locally around the stent. The localized treatment can take place at any time after implantation of the stent. For example, the stent can be locally treated after drug delivery is completed and/or after mechanical support of the vessel is no longer needed.

In some embodiments, a method of localized treatment can include releasing an acidic agent at or adjacent to a biodegradable polymer stent implanted within a bodily lumen. The acidic agent can lower the pH of bodily fluid at or adjacent to the stent. The lowered pH of the bodily fluid can increase the degradation rate of the stent.

The acidic agent can include a biodegradable or hydrophilic polymer having acidic end groups or a mild acid. For example, the acidic agent can include PEG with acid groups, PVA with acid groups, a low molecular weight PLLA with a molecular weight less than about 5000, citric acid, acetic acid, or a combination thereof. In one embodiment, the acidic agent can be a biodegradable material, such as a water soluble or biodegradable gel.

The localized treatment can be configured to lower the pH from a physiological pH to a pH that allows complete absorption of the stent in a desired time frame. For example, the change in the pH can result in absorption of the stent within a week, a month, three months, six months, or a year. The localized pH can be lowered from physiological pH to less than 6, 5, 4, or less than 3. In general, the pH can be lowered to a level to obtain a desired degree of acceleration of degradation without damaging surrounding tissue. For a given desired degradation time, the decrease in pH depends on the pH dependence of the degradation rate of the polymer.

In some embodiments, the acidic agent can be disposed within the lumen when drug delivery to the bodily lumen is completed and/or vascular support is no longer needed. Alternatively, the acidic agent can be disposed in the lumen prior to or subsequent to the time when drug delivery to the bodily lumen is completed and/or vascular support is no longer needed.

It may be desirable for the change in the pH to be sustained for a period of time to result in absorption of the stent in a desired time frame. Thus, in certain embodiments, the released acidic agent can be configured to remain at or adjacent to the implant site for a period of time. In one embodiment, the acidic agent can adhere to and coat the stent and/or the vessel wall at the implant site to allow for a sustained localized decrease in the pH. For example, an acidic gel can include a PVA or PEG gel with acid groups or a low molecular weight PLLA gel with acid groups. Such gels can adhere to tissue or a stent upon release into the lumen. In another embodiment, the acidic agent can be disposed or injected in the tissue at the vessels walls.

A soluble or biodegradable acidic agent coated on or injected into the vessel wall can decrease the local pH in a region of an implanted stent. Once the acidic agent coats or is injected into the vessel, the agent is absorbed by the bodily fluid, thus providing a sustained lowering of the pH. A sufficient amount of acidic agent should be provided to sufficiently reduce the pH for a sufficient amount of time. Since acidic agent remains in at or near the implant site for a period of time, lengthy or repeated invasive procedures may be necessary to decrease the pH.

There are a number of ways that an acidic agent can be delivered to an implant site. In general, a delivery device can be positioned within a bodily lumen at or adjacent to a biodegradable polymer stent implanted within the bodily lumen. The delivery device can be attached to a distal end of a catheter that is inserted into the bodily lumen. The proximal end of the catheter can be in fluid communication with a source of acidic agent, such as an indeflator. The proximal end, distal end, and the delivery device can be in fluid communication. The indeflator can deliver the acidic agent to the delivery device for release at the implant site.

In one embodiment, a device for delivery of an acidic agent can include a porous inflatable member or balloon in which the acidic agent is released through pores of the inflatable member. Porous balloons are known in the art, for example, a porous inflatable balloon is described in U.S. Pat. No. 6,544,223.

In another embodiment, an acidic agent can be delivered via needles projecting from the device into vessel walls at or near the stent implant site. The acidic agent can be injected directly into vessel walls through the needles at the implant site. An exemplary device known a needle injection catheter suitable for use with the present invention is the MicroSyringe™, a product of EndoBionics, Inc. (San Leandro, Calif.).

Figure 15A:
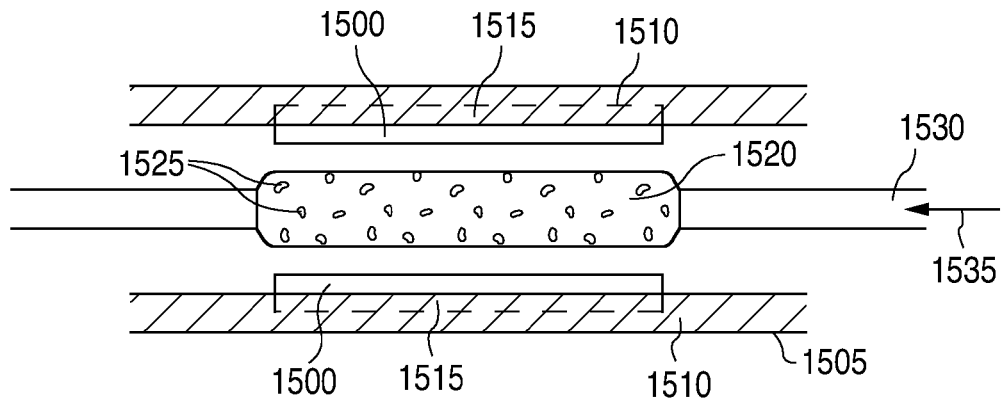
FIGS. 15A-C depict an exemplary embodiment of disposing an acidic agent at a stent implant site.
Figure 15B:
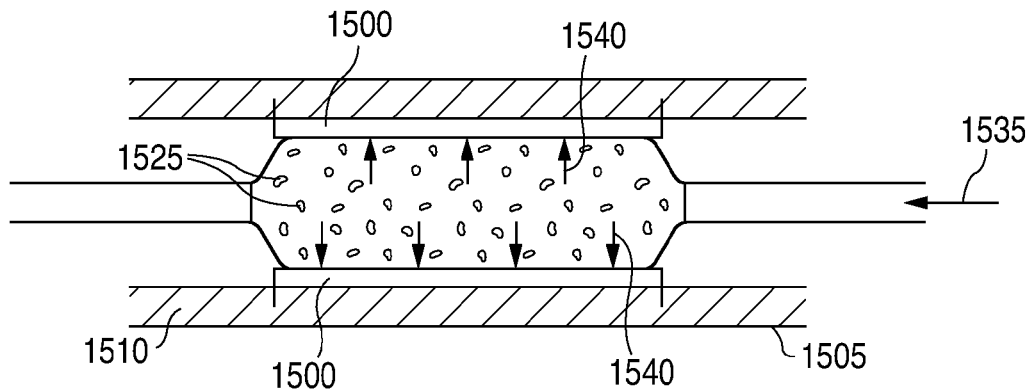
Figure 15C:
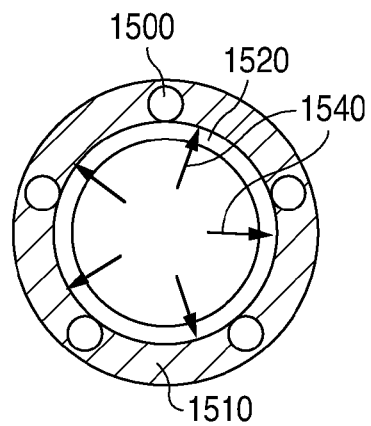

FIGS. 15A-C depict an exemplary embodiment of disposing an acidic agent at an stent implant site. FIG. 15A depicts an axial cross-section of a stent 1500 implanted in a vessel 1505 with vessel walls 1510. Due to the presence of stent 1500 in the vessel during a clinical treatment period, cell tissue has grown around at least a part 1515 of stent 1500. A porous balloon 1520 in a deflated condition with pores 1525 on catheter 1530 is disposed in vessel 1505 at the implant site.

An acidic agent can be injected into balloon 1520, as shown by an arrow 1535, from a fluid source at a proximal end (not shown) of catheter 1530.

FIG. 15B depicts balloon 1520 in an inflated condition due to acidic agent injected into balloon 1520 as shown by arrow 1535. Acidic agent is released into vessel 1505 through pores 1525, as shown by arrows 1540. FIG. 15C depicts a radial cross-section of vessel 1505 with balloon 1520 in the inflated condition. The acidic agent coats and adheres to the outer surface of vessel wall 1520. The acidic agent is injected at a pressure high enough to cause the acidic agent to permeate at least partially in and into vessel walls 1520. Once a desired amount of acidic agent is released into vessel 1505, balloon 1520 can be deflated and withdrawn from vessel 1505.

Figure 16A:
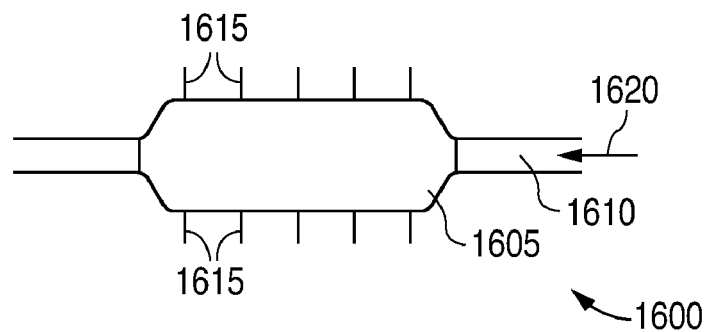
FIGS. 16A-D depict an exemplary embodiment of a device that delivers acidic agent via needles.

FIGS. 16A-D depict an exemplary embodiment of a device 1600 that delivers acidic agent via needles. In FIG. 16A, device 1600 includes a balloon 1605 disposed on a distal end of a catheter 1610. Hollow injection needles 1615 protrude from balloon 1605 and allow for fluid communication of acidic agent between the interior of balloon 1605 and the open ends of needles 1615 on the outside of balloon 1605. An acidic agent is injected into balloon 1605 as shown by an arrow 1620.

Figure 16B:
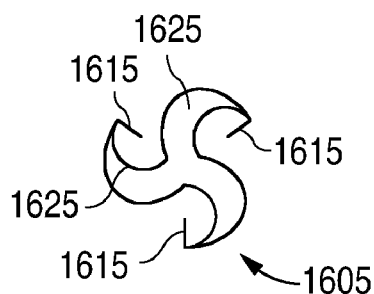

To prevent vessel injury during delivery to an implant site, balloon 1605 can be in a deflated condition with needles protruding at least partially radially inward. FIG. 16B depicts a radial cross-section of balloon 1605 with three lobes 1625 with needles 1615 pointing partially inward.

Figure 16C:
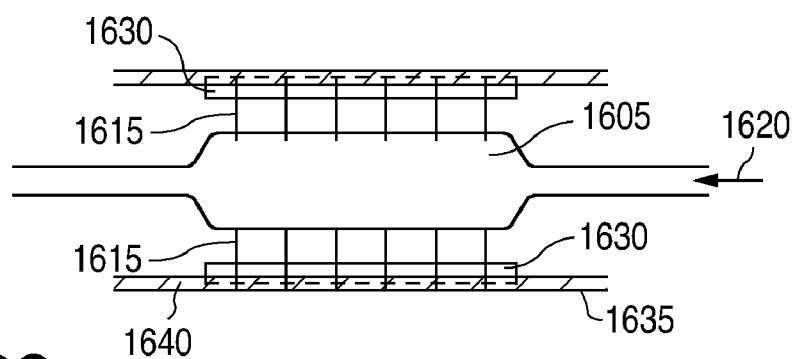
Figure 16D:
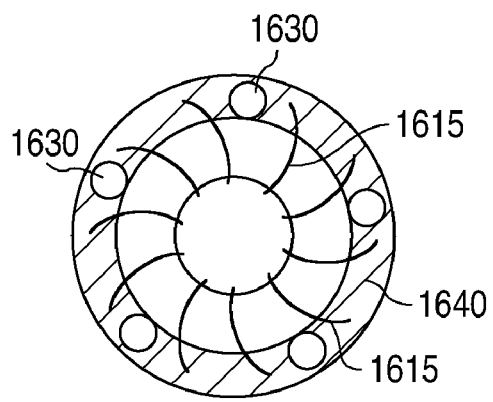

FIG. 16C depicts an axial cross-section of device 1600 disposed at an implant site. Stent 1630 is deployed in vessel 1635 and is partially encapsulated in vessel walls 1640. Acidic agent is injected into balloon 1605 and is released and injected into vessel walls 1640. FIG. 16D depicts a radial cross-section of device 1600 disposed at the implant site. As shown needles 1615 protrude into and inject acidic agent into vessel walls 1640.

In general, a stent can be made partially or completely from a biodegradable, bioabsorbable, or biostable polymer. A polymer for use in fabricating a composite implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer in device can be caused by, for example, hydrolysis and metabolic processes.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating a bodily lumen comprising:
   releasing an acidic agent at or adjacent to a hydrolytically degradable polymer stent implanted within a bodily lumen, the acidic agent lowers the pH of bodily fluid at or adjacent to the stent, the lowered pH of the bodily fluid increases the degradation rate of the stent.

2. The method of claim 1, wherein the degradable polymer has a higher degradation rate at an acidic pH as compared to a physiological pH of bodily fluid.

3. The method of claim 1, wherein the pH of the bodily fluid is lowered from a physiological pH to less than 6.

4. The method of claim 1, wherein the acidic agent is released when drug delivery to the bodily lumen is completed and/or vascular support is no longer needed.

5. The method of claim 1, wherein the acidic agent is selected from the group consisting of biodegradable polymer having acidic end groups, a hydrophilic polymer having acidic end groups, and an acid.

6. The method of claim 1, wherein the acidic agent is selected from the group consisting of poly(ethylene glycol) with acid groups, poly(vinyl alcohol) with acid groups, poly(L-lactide) with a molecular weight less than about 5000, citric acid, acetic acid, and a combination thereof.

7. The method of claim 1, wherein the hydrolytically degradable polymer comprises PLLA.

8. A method of treating a bodily lumen comprising:
   positioning a delivery device within a bodily lumen at or adjacent to a hydrolytically degradable polymer stent implanted within the bodily lumen;
   disposing an acidic agent into the delivery device;
   releasing the acidic agent from the delivery device into the bodily lumen, wherein the released acidic agent lowers the pH of the bodily fluid at or adjacent to the stent below physiological pH which increases the degradation rate of the stent.

9. The method of claim 8, wherein device comprises a porous inflatable member, the acidic agent being released through the pores of the inflatable member.

10. The method of claim 8, wherein device comprises an inflatable member, the inflatable member comprising needles protruding from an outer surface of the inflatable member into walls of the bodily lumen, the acidic agent being released through the needles of the inflatable member.

11. The method of claim 8, wherein disposing the acidic agent into device comprises injecting the acidic agent into a proximal end of a catheter, wherein the device is positioned on the distal end of the catheter, the device being in fluid communication with the catheter.

12. The method of claim 8, wherein the acidic agent is selected from the group consisting of biodegradable polymer having acidic end groups, a hydrophilic polymer having acidic end groups, and an acid.

13. The method of claim 8, wherein the acidic agent is selected from the group consisting of poly(ethylene glycol) with acid groups, poly(vinyl alcohol) with acid groups, poly(L-lactide) with a molecular weight less than about 5000, citric acid, acetic acid, and a combination thereof.

14. The method of claim 8, wherein the hydrolytically degradable polymer comprises poly(L-lactide).

15. The method of claim 8, wherein the device comprises a needle infusion catheter.

16. The method of claim 8, wherein the device comprises a porous balloon.

* * * * *